United States Patent [19]

Meguro et al.

[11] Patent Number: 4,640,916
[45] Date of Patent: Feb. 3, 1987

[54] 1,4-BENZOTHIAZINE DERIVATIVES, COMPOSITIONS CONTAINING THEM AND METHOD OF USE

[75] Inventors: Kanji Meguro, Nishinomiya; Kohei Nishikawa, Kyoto, both of Japan

[73] Assignee: Takeda Chemical Industries, Ltd., Osaka, Japan

[21] Appl. No.: 803,217

[22] Filed: Nov. 27, 1985

[30] Foreign Application Priority Data

Nov. 28, 1984 [WO] PCT Int'l Appl. .......... PCT/84/566
Apr. 16, 1985 [WO] PCT Int'l Appl. .......... PCT/85/204

[51] Int. Cl.⁴ ................... C07D 417/06; A61K 31/54
[52] U.S. Cl. .................................. 514/222; 514/225; 544/32; 544/52
[58] Field of Search ............... 544/52, 32; 514/222, 514/225; 260/243.3

[56] References Cited

U.S. PATENT DOCUMENTS 3,089,872  5/1963  Krapcho .................. 260/239.3

FOREIGN PATENT DOCUMENTS 0116368   8/1984  European Pat. Off. .
59-70679   4/1984  Japan .................................... 544/52
59-170081  9/1984  Japan .
1244481    9/1971  United Kingdom .................. 544/52

*Primary Examiner*—John M. Ford
*Attorney, Agent, or Firm*—Wenderoth, Lind & Ponack

[57] ABSTRACT

1,4-Benzothiazine derivatives of the formula;

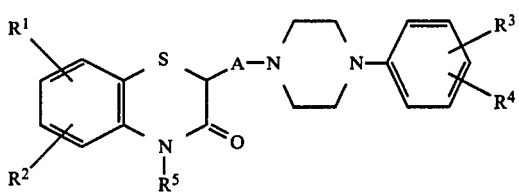

wherein $R^1$ and $R^2$ independently stand for hydrogen, halogen, a lower alkyl group, a lower alkoxy group or trifluoromethyl group, or $R^1$ and $R^2$, taken together, form a 5–7 membered ring represented by

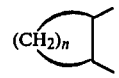

wherein n is an integer of 3 to 5 or a 5–6 membered ring represented by

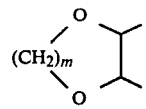

wherein m is 1 or 2, $R^3$ and $R^4$ independently stand for hydrogen, halogen, a lower alkyl group, a lower alkoxy group or trifluoromethyl group, $R^5$ stands for hydrogen or a lower alkyl group, and A stands for an alkylene group or pharmaceutically acceptable salts thereof, are useful as prophylactic or therapeutic drugs for, among others, hypertension and ischemic cardiovascular diseases.

13 Claims, No Drawings

1,4-BENZOTHIAZINE DERIVATIVES, COMPOSITIONS CONTAINING THEM AND METHOD OF USE

This invention relates to novel 1,4-benzothiazine derivatives having excellent pharmacological activities, their production and use.

No compounds which have 3-oxo-1,4-benzothiazine as the main skeletal structure have been practically used as medicines acting on the cardiovascular system. As the compounds of this type having pharmacological actions on the cardiovascular system, those having a substituted phenyl group at the 2-position are disclosed in European Patent Application Laid-Open No. 0116368A1 referring to their platelet-aggregation-inhibitory and calcium antagonistic action; and those having a group represented by

at the 2-position [wherein $R^1$ and $R^2$ may form a heterocyclic ring together with the adjacent nitrogen atom] are disclosed in Japan Patent Application Laid-Open No. 59-170081 (170081/84) referring to their diuretic and hypotensive action; respectively, and no further disclosure has yet been found.

However, 3-oxo-1,4-benzothiazine derivatives have many fields to be explored, and as to a compound having, through alkylene group, a substituent, especially 4-phenyl-1-piperazinyl group, at the 2-position and pharmacological actions thereof, nothing has been known at all.

This invention relates to novel 1,4-benzothiazine derivatives having excellent pharmacological actions, among others, strong antihypertensive and vasodilating activities. More specifically, this invention relates to:

(1) 1,4-Benzothiazine derivatives (I) of the formula;

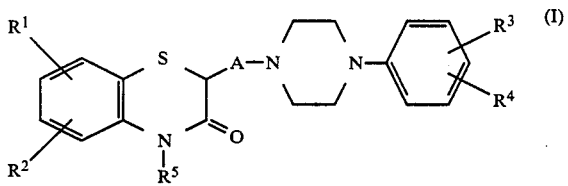

wherein $R^1$ and $R^2$ independently stand for hydrogen, halogen, a lower alkyl group, a lower alkoxy group or trifluoromethyl group, or $R^1$ and $R^2$, taken together, form a 5–7 membered ring represented by

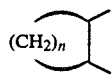

wherein n is an integer of 3 to 5 or a 5–6 membered ring represented by

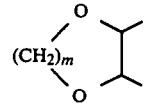

wherein m is 1 or 2, $R^3$ and $R^4$ independently stand for hydrogen, halogen, a lower alkyl group, a lower alkoxy group or trifluoromethyl group, $R^5$ stands for hydrogen or a lower alkyl group, and A stands for an alkylene group as well as acid addition salts thereof, (2) A process for producing the 1,4-benzothiazine derivatives (I) and (3) A pharmaceutical composition characteristically featured by containing the 1,4-benzothiazine derivatives (I).

In the above formula (I), the substituents represented by $R^1$, $R^2$, $R^3$ and $R^4$ may be the same or different and be present at any optional position of the benzene ring. The halogen as an example of such substituents may be fluorine, chlorine, bromine or iodine and is preferably fluorine or chlorine. When $R^3$ and $R^4$ are halogen, especially fluorine, at least one of them is preferably present at the 4-position of the benzene ring. The lower alkyls are preferably those having 1 to 4 carbon atoms, and are exemplified by methyl, ethyl, propyl, isopropyl, butyl, isobutyl, sec-butyl and t-butyl, and especially those having 1–3 carbon atoms are preferable. when $R^1$ and $R^2$ are lower alkyls adjacent to each other, they may be combined to form a 5–7 membered ring represented by

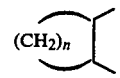

wherein n is an integer of 3 to 5. The group $-(CH_2)_n-$ is exemplified by trimethylene, tetramethylene or pentamethylene. As the lower alkoxys are preferable those having 1–3 carbon atoms, for example, methoxy, ethoxy, propoxy or isopropoxy. When $R^1$ and $R^2$ are adjacent to each other, they may be combined with each other to form a 5–6 membered ring represented by

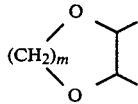

wherein m is 1 or 2. The group

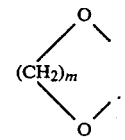

is exemplified by methylenedioxy or ethylenedioxy.

The lower alkyl shown by $R^5$ is a group of $C_{1-4}$ mentioned above, especially $C_{1-3}$ ones are preferable.

The alkylene designated by A is preferably a group of $C_{1-4}$ which may be straight-chain or branched, for example, methylene, methylmethylene, ethylene, propylene, trimethylene, 1-methyltrimethylene, 2-methyltrimethylene or tetramethylene. Especially, C$_{2-3}$ ethylene and trimethylene are preferable.

A compound of this invention representable by the formula (I) can be easily prepared by for example allowing a compound (II) of the formula;

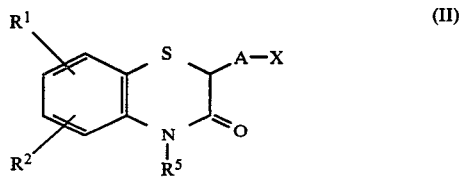

wherein X stands for a leaving group, and other symbols are of the same meaning as defined above, to react with a compound (III) of the formula;

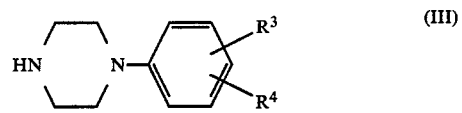

wherein all the symbols are of the same meaning as defined above.

In the formula (II), the leaving group designated by X is exemplified by halogen (e.g. chlorine, bromine, iodine, etc.), alkylsulfonyloxy (e.g. methylsulfonyloxy, ethylsulfonyloxy, etc.) or arylsulfonyloxy (e.g. phenylsulfonyloxy, tolylsulfonyloxy, etc.).

This reaction is conducted by allowing a compound (II) to react with a compound (III). This reaction can be conducted in a solvent inert to the reaction under heating, or by heating the mixture of them in the absence of a solvent. In either case, the reaction temperature ranges from about 60° C. to about 200° C., more preferably from about 80° C. to about 150° C. The solvent is exemplified by alcohols such as methanol, ethanol, propanol, 2-propanol, butanol and 2-methoxyethanol, ethers such as dioxane, tetrahydrofuran and dimethoxyethane, aromatic hydrocarbons such as benzene, toluene and xylene, ethyl acetate, acetonitrile, pyridine, N,N-dimethylformamide, dimethyl sulfoxide, etc., and a mixture of these solvents. As an acid attributable to the leaving group X is produced in this reaction, the reaction can be conducted in the presence of a suitable acid acceptor such as sodium carbonate, potassium carbonate or triethylamine, or the reaction is allowed to proceed smoothly by adding an excess amount of (III) which is allowed to act also as an acid acceptor. The amount of (III) is usually 1-3 mol. relative to 1 mole of (II), and the amount of an acid acceptor is preferably 1-3 mol. relative to 1 mol of (II).

A compound (I) wherein R$^5$ is lower alkyl can be produced by subjecting a compound (I) wherein R$^5$ is hydrogen to alkylation. This alkylation is conducted by reacting an alkylating agent in an organic solvent in the presence of a base. The solvent to be used varies with the kinds of bases employed, and is exemplified by alcohols such as methanol or ethanol, ethers such as tetrahydrofuran, dioxane, dimethoxyethane or diethyl ether, N,N-dimethylformamide, dimethyl sulfoxide, etc. The base to be used is exemplified by sodium methoxide, sodium ethoxide, potassium t-butoxide, sodium hydride, potassium hydride, sodium amide, etc., and the alkylating agent to be used is exemplified by alkyl halide (e.g. chloride, bromide, iodide, etc.), dialkylsulfate, alkylsulfonate (e.g. methanesulfonate, ethanesulfonate, benzenesulfonate, toluenesulfonate, etc.). For conducting this reaction, it is preferable to allow a compound (I) (R$^5$ is hydrogen) to react with a base in a solvent to form an anion and then to allow the resultant anion to react with an alkylating agent. The reaction temperature ranges usually from −10° C. to about 100° C., preferably from about 0° C. to about 40° C.

If required, 1,4-benzothiazine derivatives (I) can be led to acid addition salts thereof. These salts are exemplified by inorganic salts such as hydrochloride, hydrobromide, sulfate or phosphate, organic acid salts such as acetate, oxalate, malonate, succinate, malate, fumarate, maleate or tartrate, and sulfonates such as methanesulfonate, benzenesulfonate or toluenesulfonate.

The 1,4-benzothiazine derivatives (I) as well as salts thereof are novel compounds and display strong vasodilating activity, noradrenaline-receptor-blocking activity, hypotensive activity due to intracellular calcium antagonism, activity of ameliorating cerebral circulation, etc. in mammals (e.g. rat, rabbit, dog, cat and man). Especially, it is a great characteristic feature of the compounds of this invention that they display intracellular calcium antagonism. Contraction of smooth muscle requires calcium ion (Ca$^{++}$), and this Ca$^{++}$ includes (1) that which flows in the cells through so-called Ca$^{++}$ channel, (2) that which is liberated from the intracellular Ca$^{++}$ store site, and (3) that which flows in the cells through the receptor-dependent channel. A Ca$^{++}$ channel blocker such as nifedipine hardly acts on (2) and (3). As the compounds acting on (2) and showing antagonism against intracellular Ca$^{++}$, there have been known e.g. trifluoperazine, TMB-8 and W-7, but the latter two compounds are weak in their action and do not display antihypertensive action in vivo. Trifluoperazine has not been practically used as an antihypertensive agent or an ameliorant of cerebral circulation, due to its side effects e.g. on the central nervous system. The compounds of this invention having a remarkable intracellular Ca$^{++}$ antagonism are capable of inhibiting contraction caused in any of the cases (1), (2) and (3) mentioned above, displaying pharmacological activities in a broader area than that where a Ca$^{++}$ channel blocker is effective. Besides vasodilating action, they also show bronchodilating action, and are expected to be of use as an antiasthmatic drug. The compounds (I) of this invention also have protective action on the damages of ischemic heart, brain and kidney. The compounds (I) show low toxicity and less side effects including orthostatic hypotension often observed by administration of prazosin, one of the typical α-adrenoceptor blockers, and thus are very useful for treatment and protection of hypertension and ischemic cardiovascular diseases such as cerebral infarction, transient ischemic attack, myocardial infarction, acute renal failure and nephritis.

In the use of the compound (I) or its salt as the above-mentioned pharmaceuticals, it can be administered orally or otherwise in such dosage forms as powders, granules, tablets, capsules, injections, etc. which may be prepared by mixing with a pharmaceutically acceptable carrier, excipient or diluent. Although the dosage should vary with such factors as the route of administration, and the condition, body weight and age of the patient, etc., 0.05–10 mg/kg body weight/day, preferably 0.1–5 mg/kg body weight/day, for instance, is orally administered divided into 1 to several times a day, to an adult patient with hypertension.

The starting compound (II) of this invention can be prepared, for example, by the following processes.

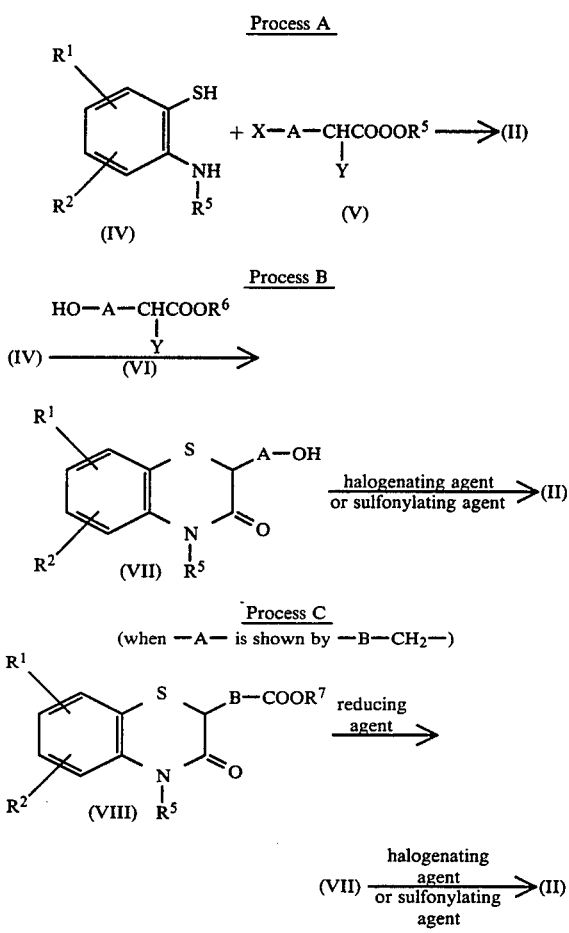

[In the above formulae, Y stands for halogen, $R^6$ and $R^7$ each stands for hydrogen or lower alkyl, B stands for a bond arm or alkylene, and other symbols are of the same meaning as defined above.]

The lower alkyl groups shown by $R^6$ and $R^7$ in the above formulae (V), (VI) and (VIII) are exemplified by those having 1–4 carbon atoms like those representable by $R^1$–$R^5$. The halogen shown by the formulae (V) and (VI) is exemplified by chlorine, bromine or iodine. When B in the formula (VIII) stands for a bond arm, the 2-position of 1,4-benzothiazine is necessarily combined directly to $COOR^7$, and, when B stands for alkylene, carbon number of the alkylene is always less than that of A by one, and —B—$CH_2$— is necessarily equal to —A—. The following are brief explanations of the respective processes.

Process A

According to this process, a compound (II) can be prepared in one step by allowing a compound (IV) to react with a compound (V). This reaction is usually conducted in a suitable solvent at temperatures ranging from about 0° C. to about 100° C. The solvent is exemplified by alkanols such as methanol, ethanol, propanol or 2-propanol; ethers such as tetrahydrofuran, dioxane or dimethoxyethane; acetonitrile and N,N-dimethylformamide.

Process B

A compound (IV) is allowed to react with a compound (VI) to give a compound (VII), which is then subjected to halogenation or sulfonylation to produce a compound (II). The reaction between (IV) and (VI) can be conducted exactly in the same manner as that between (IV) and (V) mentioned above. The halogenating agent to be used for the halogenation of a compound (VII) is exemplified by thionyl chloride, phosphorus oxychloride, phosphorus tribromide, etc., and the sulfonylating agent is exemplified by methanesulfonyl chloride, benzenesulfonyl chloride, toluenesulfonyl chloride, etc. The halogenation of (VII) is usually conducted at about 15° C. to about 100° C., in an appropriate solvent exemplified by dichloromethane, chloroform, benzene, toluene, etc. The reaction between (VII) and the sulfonylating agent can be conducted under conditions similar to those used in the halogenation, and, if necessary, it may be conducted more advantageously in the presence of a base such as triethylamine, pyridine, etc.

Process C

In this process, a compound (VIII) is first subjected to reduction to give a compound of (VII), which is allowed, in a manner similar to that in Process B, to react with a halogenating agent or a sulfonylating agent to produce a compound (II). The reduction of the compound (VIII) can be conducted by the use of e.g. sodium borohydride in a solvent such as methanol, ethanol, etc. or lithium aluminum hydride in a solvent such as ethyl ether, tetrahydrofuran, etc. at a temperature ranging from about 0° C. to about 100° C. The starting compound (VIII) can be synthesized, for example, by the reaction scheme shown below:

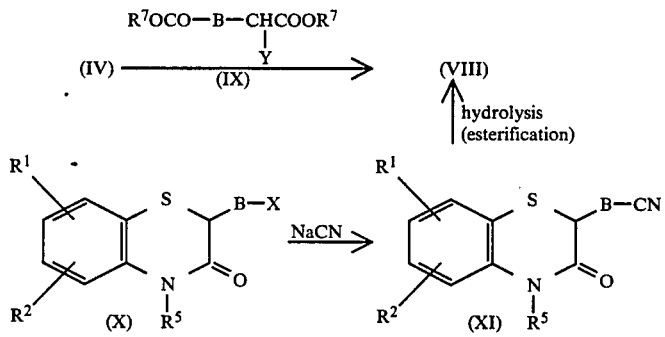

[In the above scheme, all the symbols are of the same meaning as defined above.]

The reaction between (IV) and (IX) is conducted in the same manner as that between (IV) and (V) mentioned above to give (VIII). Alternatively, (VIII) can be obtained by allowing (X) to react with sodium cyanide to give (XI), which is then subjected to hydrolysis, and, if necessary, further to esterification. The reaction between (X) and sodium cyanide can be conducted in a suitable solvent (e.g. methanol, ethanol, N,N-dimethylformamide, dimethyl sulfoxide, etc.) at about 0° C.-100° C. The hydrolysis of (XI) can be conducted by using a mineral acid (e.g. hydrochloric acid, hydrobromic acid, sulfuric acid, etc.) or an alkali (e.g. sodium hydroxide, potassium hydroxide, etc.) in a suitable solvent (e.g. methanol, ethanol, 2-methoxyethanol, etc.) at about 60° C. to about 120° C. The resultant carboxylic acid can be converted to a desired ester by a per se known esterification process. Alternatively, (XI) is processed with hydrogen chloride or hydrogen bromide in an appropriate alcohol in the presence of a small volume of water to give (VIII) in one step.

The following are the results of pharmacological tests indicating the effectiveness of compounds (I) of this invention.

1. Vasodilating Action

A spiral strip of aorta of a rabbit (2-3 mm width, about 3 cm length) was allowed to equilibrate by hanging under 2 g force in a Krebs-Henseleit solution. The solution was saturated with a mixture gas of 97% $O_2$—3% $CO_2$ which was warmed to 37° C. Inhibitory actions of compounds ($10^{-5}$M) of this invention against contraction of the aorta strip caused by KCl (60 mM), norepinephrine (NE) ($10^{-6}$M) or serotonin (5—HT) ($10^{-6}$M), by treating the strip with a compound of this invention 15 minutes before the test, are shown in Table 1 as inhibitory percent.

TABLE 1

| Compound | Inhibitory percent against contraction (%) | | |
|---|---|---|---|
| | KCl | NE | 5-HT |
| 1 | 50 | 100 | — |
| 2 | 70 | 100 | 97 |
| 3 | 53 | 100 | — |
| 4 | 18 | 100 | 12 |
| 5 | 10 | 100 | 100 |
| 6 | 26 | 100 | 91 |
| 7 | 77 | 60 | — |
| 8 | 34 | 100 | 18 |
| 9 | 40 | 100 | 44 |
| 10 | 45 | 100 | — |
| 11 | 70 | 95 | 67 |
| 12 | 41 | 100 | 96 |
| 13 | 40 | 100 | 92 |
| 14 | 50 | 100 | — |
| 15 | 40 | 100 | 20 |
| 16 | 33 | 100 | 70 |
| 17 | 11 | 100 | — |
| 18 | 50 | 100 | — |
| 19 | 55 | 100 | — |
| 21 | 32 | 100 | 56 |
| 22 | 62 | 100 | 15 |
| 23 | 40 | 100 | — |
| 24 | 20 | 100 | 66 |
| 25 | 10 | 100 | 84 |
| 26 | 60 | 60 | — |
| 27 | 20 | 100 | 100 |
| 28 | 15 | 100 | 100 |
| 29 | 15 | 96 | 73 |
| 30 | 42 | 90 | 100 |
| 31 | 40 | 100 | 62 |
| 32 | — | 100 | 88 |
| 36 | 15 | 100 | 100 |
| 38 | 30 | 100 | — |

2. Intracellular $Ca^{++}$ Antagonism

A spiral strip of aorta of a rabbit (2-3 mm width, about 3 cm length) was allowed to equilibrate by hanging under 2 g force in a Krebs-Henseleit solution. The solution was saturated with a mixture gas 97% $O_2$—3% $CO_2$, which was warmed to 37° C. The strip was moved into another Krebs-Henseleit solution containing $Ca^{++}$ OmM and EGTA 5 mM. Five minutes later, phenylephrine ($10^{-6}$M) was added on the solution. The resulting contraction of the strip was made as the index of the contraction depending on intracellular $Ca^{++}$. The inhibitory percent on this contraction by addition of the compounds of this invention is shown in Table 2.

TABLE 2

| Compound (Example No.) | concentration (M) | Inhibitory percent (%) |
|---|---|---|
| 1 | $10^{-6}$ | 66 |
| 11 | $10^{-6}$ | 97 |
| 12 | $10^{-6}$ | 100 |
| 14 | $10^{-6}$ | 100 |
| 15 | $10^{-6}$ | 30 |
| 22 | $10^{-6}$ | 100 |
| TMB-8 | $10^{-4}$ | 58 |

3. Antihypertensive Action

Male 12 to 13 weeks old spontaneously hypertensive rats with about 200 mm Hg of blood pressure were used in groups of 3 individuals. Mean arterial blood pressures of these animals were measured by the tail-cuff method, then the animals were orally given 3-60 mg/kg of each test compound of this invention as 2 ml of its suspension in gum arabic. Blood pressure measurements were made again one hour after administration of each test compound. The antihypertensive effects (difference of blood pressure before and after medication, $\Delta$ mm Hg) are shown in Table 3.

TABLE 3

| Compound (Example No.) | Dose (mg/Kg) | Antihypertensive effect ($\Delta$mmHg) |
|---|---|---|
| 1 | 30 | 35 |
| 2 | 30 | 43 |
| 5 | 10 | 49 |
| 6 | 10 | 64 |
| 9 | 60 | 35 |
| 10 | 30 | 33 |
| 11 | 30 | 49 |
| 12 | 60 | 49 |
| 13 | 60 | 36 |
| 14 | 30 | 26 |
| 17 | 30 | 26 |
| 22 | 30 | 39 |
| 23 | 30 | 48 |
| 25 | 30 | 66 |
| 26 | 30 | 26 |
| 28 | 30 | 29 |
| 29 | 10 | 38 |
| 30 | 30 | 40 |
| 32 | 60 | 30 |
| 38 | 30 | 32 |
| 41 | 30 | 23 |
| 42 | 30 | 28 |
| 45 | 30 | 30 |
| 46 | 3 | 33 |
| 47 | 30 | 35 |

4. Protective action on ischemic cardiovascular tissue damages 4-1. Effect on the ischemia-reperfusion-induced ventricular arrythmia in rats Male Sprague-Dawley rats, 9 to 10 week old, were orally given the compounds or tap water at a volume of 5 ml/kg. After 1 hour, rats were anesthetized with sodium pentobarbital (50 mg/kg, i.p.), and left anterior descending coronary artery was occluded for 5 min. with a silk thread under ventilation. The incidences of ventricular tachycardia (VT), ventricular fibrillation (VF) and cardiac arrest (CA) occurred for 10 min. after reperfusion of the blood were calculated.

As shown in Table 4, the compound of Example 48 at 1, 3 and 10 mg/kg, p.o. and the compound of Example 46 at 0.3, 1, 3 and 10 mg/kg, p.o. inhibited the incidences of VT, VF and CA in a dose-dependent manner.

TABLE 4

| Compound (Example No.) | Dose mg/kg, p.o. | VT | VF | CA |
|---|---|---|---|---|
| Control | — | 20/20 | 20/20 | 12/20 |
| 48 | 1 | 7/10* | 5/10* | 3/10 |
|  | 3 | 4/9** | 3/9** | 1/9* |
|  | 10 | 1/6** | 1/6** | 0/6* |
| Control | — | 12/12 | 12/12 | 9/12 |
| 46 | 0.3 | 12/19 | 9/19* | 9/19 |
|  | 1 | 7/12* | 5/12** | 0/12* |
|  | 3 | 5/12** | 2/12** | 0/12* |
|  | 10 | 1/4* | 1/4* | 0/4* |

The number of denominator shows the number of rats used and that of numerator shows the number of rats which induced the changes in cardiac function.
$X^2$-test: *P < 0.05, **P < 0.01

4-2. Effect on the ischemic seizure induced by bilateral carotid artery occlusion in spontaneously hypertensive rats Male spontaneously hypertensive rats, 20 to 22 week old, were orally given the compounds or tap water at a volume of 5 ml/kg. After 1 hour, the carotid artery was bilaterally occluded by use of silk thread under anesthesia with sodium pentobarbital (50 mg/kg, i.p.). The length of time until the ischemic seizure such as convulsion and jumping was observed was measured, immediately after the occlusion of carotid artery.

As shown in Table 5, the compound of Example 48 at 1, 3 and 10 mg/kg, p.o. and the compound of Example 46 at 0.3, 1 and 3 mg/kg, p.o. prolonged the time of the beginning of the ischematic seizure in a dose-dependent manner.

TABLE 5

| Compound (Example No.) | Dose mg/kg, p.o. | Number of rats | Time toward ischemic seizure (min.) |
|---|---|---|---|
| Control | — | 10 | 139 ± 9 |
| 48 | 1 | 10 | 167 ± 8* |
| Control | — | 5 | 152 ± 14 |
| 48 | 3 | 5 | 214 ± 22* |
| Control | — | 7 | 132 ± 14 |
| 48 | 10 | 5 | 275 ± 22** |
| Control | — | 5 | 153 ± 8 |
| 46 | 0.1 | 5 | 167 ± 13 |

TABLE 5-continued

| Compound (Example No.) | Dose mg/kg, p.o. | Number of rats | Time toward ischemic seizure (min.) |
|---|---|---|---|
| Control | — | 10 | 143 ± 7 |
| 46 | 0.3 | 11 | 190 ± 11 |
| Control | — | 5 | 150 ± 6 |
| 46 | 1 | 5 | 217 ± 11** |
| 46 | 3 | 5 | 279 ± 18** |

Student's t-test: *P < 0.05, **P < 0.01

4-3. Effect on the ischemic acute renal failure in rats

The left renal artery of male Sprague-Dawley rats, 6 week old, was clamped for 1 hour under anesthesia with sodium pentobarbital (50 mg/kg, i.p.). The compounds or water was orally given 1 hour before the occlusion. The compounds were again given 20 hour after the reperfusion of the blood. Twenty four hour after the reperfusion, the blood was obtained from the abdominal aorta under anesthesia for measurement of plasma urea nitrogen (BUN).

As shown in Table 6, the compound of Example 48 at 10 mg/kg and the compound of Example 46 at 1 and 3 mg/kg inhibited the increase in BUN.

TABLE 6

| Compound (Example No.) | Dose mg/kg, p.o. | Number of rats | BUN mg/dl |
|---|---|---|---|
| Control | — | 10 | 20.3 ± 0.6 |
| 48 | 3 | 9 | 18.9 ± 0.6 |
| Control | — | 23 | 22.8 ± 1.0 |
| 48 | 10 | 20 | 16.9 ± 0.7** |
| Control | — | 5 | 20.4 ± 0.4 |
| 46 | 1 | 5 | 18.0 ± 0.7* |
| Control | — | 18 | 25.1 ± 0.8 |
| 46 | 3 | 17 | 19.6 ± 0.8** |

Student's-test: *P < 0.05, **P < 0.01

The melting point values shown in the following examples were measured by the hot plate method and are uncorrected.

EXAMPLE 1

In 10 ml of ethyl acetate were dissolved 628 mg of 2-(3-bromopropyl)-6,7-dimethyl-2H-1,4-benzothiazin-3(4H)-one and 721 mg of 1-(4-fluorophenyl)piperazine. The solution was concentrated and the concentrate was stirred at 110° C. for one hour, diluted with water, and extracted with ethyl acetate. The ethyl acetate layer was washed with water, dried over MgSO$_4$ and concentrated to give 2-[3-[4-(4-fluorophenyl)-1-piperazinyl]-propyl]-6,7-dimethyl-2H-1,4-benzothiazin-3(4H)-one (650 mg, 78.6%). Recrystallization from methanol gave colorless prisms, m.p. 161°–162° C.

IR(Nujol)cm$^{-1}$: 3190, 1665.

NMR δ(ppm)in CDCl$_3$: 1.4–2.1(4H, m), 2.19(6H, s), 2.28(2H, t, J=6), 2.43–2.62(4H, m), 3.00–3.10 (4H, m), 3.41(1H, m), 6.63–7.03(6H, m), 8.87(1H, broad).

Elemental Analysis for C$_{23}$H$_{28}$FN$_3$OS, Calcd: C 66.80; H 6.82; N 10.16, Found: C 67.00; H 6.92; N 10.12.

EXAMPLES 2–11

By a process similar to that in Example 1, the compounds shown in Table 7 were produced.

TABLE 7

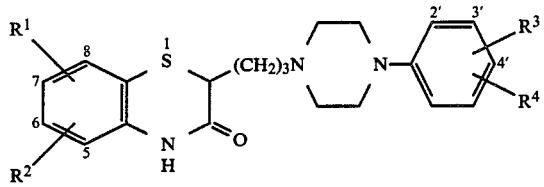

| Example No. | R¹ | R² | R³ | R⁴ | Melting point (°C.) | Recrystallization solvent | Yield |
|---|---|---|---|---|---|---|---|
| 2 | H | H | H | H | 137–138 | Ethyl acetate | 59.0 |
| 3 | H | H | H | 4'-F | 161–162 | Methanol | 75.7 |
| 4 | H | 5-OCH₃ | H | 2'-OCH₃ | 123–124 | Ethyl acetate-hexane | 72.4 |
| 5 | H | 7-OCH₃ | H | H | 140–141 | Ethyl acetate-hexane | 72.7 |
| 6 | H | 7-OCH₃ | H | 2'-OCH₃ | 123–124 | Ethyl acetate-hexane | 62.5 |
| 7 | H | 5-CH₃ | H | 4'-CH₃ | 149–150 | Ethyl acetate | 79.6 |
| 8 | H | 6-Cl | H | 2'-OCH₃ | 117–118 | Ethyl acetate-hexane | 59.8 |
| 9 | H | 7-Cl | H | 2'-OCH₃ | 191–192 | Methanol-dichloromethane | 77.7 |
| 10 | H | 6-CF₃ | H | 4'-F | 160–161 | Methanol | 68.4 |
| 11 | 5-CH₃ | 7-CH₃ | H | 4'-F | 163–164 | Ethyl acetate | 66.1 |

EXAMPLE 12

In 30 ml of ethyl acetate were dissolved 3.0 g of 2-(3-bromopropyl)-5-methyl-2H-1,4-benzothiazin-3(4H)-one and 3.6 g of 1-(4-fluorophenyl)piperazine.

The solution was concentrated and the concentrate was stirred at 110° C. for one hour.

The mixture was partitioned between 50 ml of water and 100 ml of ethyl acetate.

The ethyl acetate layer was separated, washed with water and dried over MgSO₄.

After concentration, the resultant crude product was subjected to a column chromatography on silica-gel (100 g). From the eluate with hexane-ethyl acetate (1:1, v/v) was obtained 2-[3-[4-(4-fluorophenyl)-1-piperazinyl]propyl]-5-methyl-2H-1,4-benzothiazin-3(4H)-one (2.6 g, 55.1%). Recrystallization from methanol gave colorless prisms, m.p. 116°–117° C.

IR(Nujol)cm⁻¹: 3220, 1655.

NMR δ(ppm)in CDCl₃: 1.5–2.1(4H, m), 2.30(3H, s), 2.3–2.59(6H, m) 2.99–3.11(4H, m), 3.01–3.49(1H, m), 6.7–7.22(7H, m).

Elemental Analysis for $C_{22}H_{26}FN_3OS$, Calcd.: C 66.14; H 6.56; N 10.52, Found: C 66.17; H 6.62; N 10.49.

The crystals obtained above were dissolved in methanol and treated with a methanol solution of hydrogen chloride to give crystals of the dihydrochloride. Recrystallization from methanol gave colorless prisms, m.p. 161°–163° C.

Elemental Analisis for $C_{22}H_{26}FN_3OS.2HCl$, Calcd.: C 55.93; H 5.97; N 8.89, Found: C 55.56; H 5.99; N 8.72.

EXAMPLES 13–24

By a process similar to that in Example 12, the compounds shown in Table 8 were produced.

TABLE 8

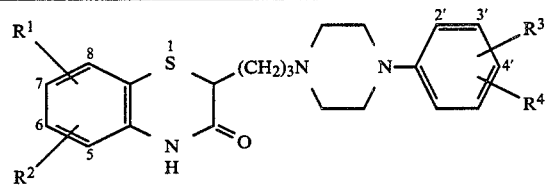

| Example No. | R¹ | R² | R³ | R⁴ | Melting point (°C.) | Recrystallization solvent | yield (%) |
|---|---|---|---|---|---|---|---|
| 13 | H | 5-CH₃ | H | H | 235–236 (Decomposition)HCl | Methanol | 56.2 |
| 14 | H | 5-CH₃ | H | 3'-Cl | 204–206 2HCl.½H₂O | Methanol-ether | 53.2 |
| 15 | H | 5-CH₃ | H | 4'-Cl | 129–120 2HCl | Methanol | 55.2 |
| 16 | H | 5-CH₃ | H | 2'-OCH₃ | 168–169 2HCl | Methanol | 64.8 |
| 17 | H | 5-CH₃ | H | 2'-CH₃ | 240–242 HCl | Methanol | 59.2 |
| 18 | H | 5-CH₃ | H | 3'-CH₃ | 142–144 2HCl.½H₂O | Methanol | 65.0 |
| 19 | H | 5-CH₃ | H | 3'-CF₃ | 132–134 2HCl | Methanol | 42.9 |
| 20 | H | 5-CH₃ | 3'-OCH₃ | 4'-OCH₃ | 187–190 2HCl | Methanol | 54.4 |
| 21 | H | 7-CH₃ | H | 2'-OCH₃ | 164–165 2HCl.½H₂O | Methanol | 64.4 |
| 22 | 5-CH₃ | 7-CH₃ | H | 2'-OCH₃ | 159–160 2HCl | Methanol-dichloromethane | 58.2 |
| 23 | 6-CH₃ | 7-CH₃ | H | 2'-OCH₃ | 203–205 2HCl | Methanol-chloroform | 67.0 |
| 24 | H | 5-OCH₃ | H | H | 209–211 | Methanol-ether | 72.4 |

TABLE 8-continued

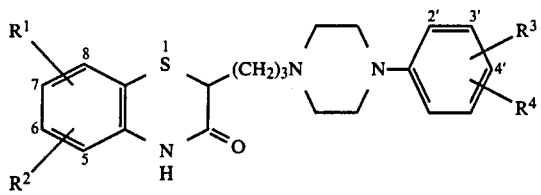

| Example No. | R¹ | R² | R³ | R⁴ | Melting point (°C.) | Recrystallization solvent | yield (%) |
|---|---|---|---|---|---|---|---|
| | | | | | (Decomposition)2HCl | | |

EXAMPLE 25

In 10 ml of dimethylformamide were dissolved 1.6 g of 2-(3-chloropropyl)-2H-1,4-benzothiazin-3(4H)-one and 2.55 g of 1-(2-methoxyphenyl)piperazine. The solution was stirred at 100° C. for 1.5 hour. The reaction mixture was poured into ice-water, and extracted with ethyl acetate. The ethyl acetate layer was washed with water, dried over MgSO₄, then concentrated under reduced pressure. The concentrate was subjected to a column chromatography on silica-gel (150 g). From the eluate with hexane-acetone (2:1, v/v) was obtained 0.7 g of 2-[3-[4-(2-methoxyphenyl)-1-piperazinyl]propyl]-2H-1,4-benzothiazin-3(4H)-one as an oily substance. The 3/2 oxalate of this product was obtained as crystals, which were recrystallized from methanol and dichloromethane to give colorless prisms. The yield was 470 mg (13.3%), m.p. 202°–204° C.

IR(Nujol)cm⁻¹: 3180, 2400–3000(broad), 1720, 1665.

NMR δ(ppm)in DMSO—d₆: 1.4–2.1(4H, m), 2.95–3.79(11H, m) 3.80(3H, s), 6.87–7.33(8H, m), 10.6(1H, broad).

Elemental Analysisi for $C_{22}H_{27}N_3O_2S.3/2C_2H_2O_4$, Calcd.: C 56.38; H 5.68; N 7.89, Found: C 56.10; H 5.63; N 7.87.

EXAMPLE 26

In 20 ml of ethyl acetate were dissolved 1.36 g of 2-(2-bromoethyl)-2H-1,4-benzothiazin-3(4H)-one and 1.8 g of 1-(4-fluorophenyl)piperazine. The solvent was evaporated off, and the residue was stirred at 110° C. for one hour. The reaction product was extracted with ethyl acetate, and the extract was washed with water and dried over MgSO₄. The crystals obtained by evaporation of the solvent were recrystallized from methanol to give 2-[2-[4-(4-fluorophenyl)-1-pyrazinyl]ethyl]-2H-1,4-benzothiazin-3(4H)-one as prisms, m.p. 158°–159° C. The yield was 0.94 g (50.5%).

IR(Nujol)cm⁻¹: 3210, 1665.

NMR δ(ppm)in CDCl₃: 2.53–2.62(6H, m), 3.02–3.11(4H, m), 3.62(1H, d.d, J=7 and 8 Hz), 6.72–7.34(8H, m), 9.46(1H, broad).

Elemental Analysis for $C_{20}H_{22}FN_3OS$, Calcd.: C 64.67; H 5.97; N 11.31, Found: C 64.82; H 6.02; N 11.25.

EXAMPLES 27–29

By a process similar to that in Example 26, the compounds shown in Table 9 were synthesized.

TABLE 9

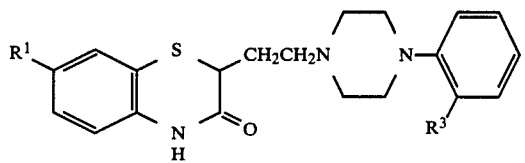

| Example No. | R¹ | R³ | Melting point (°C.) | Recrystallization solvent | Yield (%) |
|---|---|---|---|---|---|
| 27 | H | H | 145–146 | Methanol | 62.3 |
| 28 | H | OCH₃ | 162–163 | Methanol | 65.2 |
| 29 | OCH₃ | H | 157–158 | Ethylacetate-hexane | 72.5 |

EXAMPLE 30

To 15 ml of dimethylformamide were added 1.21 g of 2-(2-chloroethyl)-4-methyl-2H-1,4-benzothiazin-3(4H)-one, 1.08 g of 1-(4-fluorophenyl)piperazine, 0.69 g of potassium carbonate and 0.05 g of sodium iodide. The mixture was stirred at 100° C. for 4 hours. The reaction solution was poured into ice-water and extracted with dichloromethane. The dichloromethane layer was washed with water and dried (MgSO₄). Then, the solvent was evaporated off. The residue was subjected to a column chromatography on silica-gel (130 g). From the eluate with hexane-ethyl acetate (1:1, v/v) was obtained 2-[2-[4(4-fluorophenyl)-1-piperazinyl]ethyl]-4-methyl-2H-1,4-benzothiazin-3(4H)-one as an oily substance. This product was treated with methanol saturated with hydrogen chloride to give crystals of its hydrochloride. The yield was 0.99 g (43.2%). Recrystallization from methanol-ether gave prisms, m.p. 202°–204° C.

IR(Nujol)cm⁻¹: 2520, 2430, 1660.

NMR δ(ppm)in DMSO—d₆: 1.6–2.4(2H, m), 3.5–3.64(10H, m) 3.71–3.87(1H, m), 3.78(3H, s), 6.3(2H, broad), 6.7–7.47(8H, m), 11.5(1H, broad).

Elemental Analysis for $C_{21}H_{24}FN_3OS.2HCl$, Calcd.: C 55.02; H 5.72; N 9.17, Found: C 55.21; H 5.84; N 9.21.

EXAMPLES 31–33

By a process similar to that in Example 30, the compounds shown in Table 10 were synthesized.

TABLE 10

[Structure: benzothiazinone with N-CH3, bearing CH2CH2N-piperazinyl-phenyl(R³,R⁴) substituent]

| Example No. | R³ | R⁴ | Melting point (°C.) (salt) | Recrystallization solvent | Yield (%) |
|---|---|---|---|---|---|
| 31 | H | H | 208–209 (HCl) | Ethanol | 32.3 |
| 32 | OCH₃ | H | 149–151 (2HCl.½H₂O) | Methanol-ether | 50.4 |
| 33 | H | Cl | 220–222 (HCl) | Methanol-ether | 32.1 |

EXAMPLE 34

In 20 ml of ethyl acetate were dissolved 1.20 g of 2-(3-bromopropyl)-4-methyl-2H-1,4-benzothiazin-3(4H)-one and 1.44 g of 1-(4-fluorophenyl)piperazine.

The solvent was evaporated off, and the residue was stirred at 110° C. for one hour. The reaction mixture was extracted with ethyl acetate.

The extract was washed with water, dried (MgSO₄), and concentrated. The concentrate was subjected to a column chromatography on silica-gel (40 g). From the eluate with hexane-ethyl acetate (1:1, v/v) was obtained 2-[3-[4-(4-fluorophenyl)-1-piperazinyl]propyl-4-methyl-2H-1,4-benzothiazin-3(4H)-one as crystals. The yield was 1.00 g (62.5%). Recrystallization from ethyl acetate-hexane gave colorless prisms, m.p. 103°–104° C.

IR(Nujol)cm⁻¹: 1645.

NMR δ(ppm)in CDCl₃: 1.4–2.1(4H, m), 3.01–3.09 2.3–2.59(6H, m), (4H, m), 3.38–3.52(1H, m), 3.43(3H, s), 6.73–7.41(8H, m).

Elemental Analysis for $C_{22}H_{26}FN_3OS$, Calcd.: C 66.14; H 6.56; N 10.52, Found: C 66.33; H 6.63; N 10.57.

EXAMPLE 35

To a solution of 193 mg of 2-[3-[4-(4-fluorophenyl)-1-piperazinyl]propyl]-2H-1,4-benzothiazine in 2 ml of dimethylformamide was added 20 mg of 60% sodium hydride in oil. The mixture was stirred at room temperature for 30 minutes and cooled with ice. To the resultant was added 0.07 ml of methyl iodide, and the mixture was stirred for further one hour. The reaction mixture was poured into water, and extracted with ethyl acetate. The extract was washed with water, dried (MgSO₄) and concentrated to give 2-[3-[4-(4-fluorophenyl)-1-piperazinyl]propyl]-4-methyl-2H-1,4-benzothiazin-3(4H)-one as crystals. Recrystallization from ethyl acetate and hexane gave prisms, m.p. 103°–104° C. The yield was 84 mg (42%). IR and NMR spectra of this product was in agreement with those of the compound obtained in Example 34.

EXAMPLE 36

In a solution of 1.0 g of 2-[2-[4-(2-methoxyphenyl)-1-piperazinyl]ethyl]-2H-1,4-benzothiazin-3(4H)-one, in 10 ml of dimethylformamide, was added 120 mg of 60% sodium hydride in oil at room temperature with stirring. The mixture was stirred for 10 minutes and 480 mg of ethyl iodide was added thereto. The whole mixture was stirred for further two hours, poured into ice-water and extracted with ethyl acetate. The ethyl acetate layer was washed with water and dried (MgSO₄), and concentrated. The residue was subjected to a column chromatography on silica-gel (50 g). From the eluate with hexane-ethyl acetate (2:1, v/v) was obtained 4-ethyl-2-[2-[4-(2-methoxyphenyl)-1-piperazinyl]ethyl]-2H-1,4-benzothiazin-3(4H)-one as an oily substance (0.60 g). This product was crystallized as the hydrochloride. The yield was 0.50 g (39%). Recrystallization from methanol-ether gave colorless prisms, m.p. 142°–144° C.

IR(Nujol)cm⁻¹: 2450–2200, 1660.

NMR δ(ppm)in DMSO—d₆: 1.13(3H, t, J=7 Hz), 1.7–2.4(2H, m), 2.9–3.87(11H, m), 3.79(3H, s), 4.02(2H, q, J=7 Hz), 6.84–7.0(8H, m).

Elemental Analysis for $C_{23}H_{29}N_3OS.2HCl.\tfrac{1}{2}H_2O$, Calcd.: C 55.98; H 6.54; N 8.51, Found: C 56.18; H 6.47; N 8.62.

EXAMPLE 37

A solution of 427 mg of 2-chloromethyl-2H-1,4-benzothiazin-3(4H)-one and 720 mg of 1-(4-fluorophenyl)-piperazine in 10 ml of ethylacetate was heated to remove the solvent. The residue was stirred at 110° C. for one hour. The reaction mixture was cooled and diluted with water, whereupon crystals of 2-[4-(4-fluorophenyl)-1-piperazinyl]methyl-2H-1,4-benzothiazin-3(4H)-one precipitated. The crystals were collected by filtration and washed with water and cold methanol. Recrystallization from methanol-dichloromethane gave prisms. The yield was 450 mg (62.9%), m.p. 192°–193° C.

IR(Nujol)cm⁻¹: 3200, 1665.

NMR δ(ppm)in DMSO—d₆: 2.47–2.8(6H, m), 2.97–3.24(4H, m), 3.86(1H, t, J=7 Hz), 6.78–7.36(8H, m), 10.53(1H, broad).

Elemental Analysis for $C_{19}H_{20}FN_3OS$, Calcd.: C 63.84; H 5.64; N 11.76, Found: C 63.93; H 5.67; N 11.83.

EXAMPLE 38

In 10 ml of ethyl acetate were dissolved 435 mg of 2-(4-chlorobutyl)-2H-1,4-benzothiazin-3(4H)-one and 613 mg of 1-(4-fluorophenyl)piperazine. The solvent was evaporated off, and the residue was stirred at 110° C. for one hour. The reaction mixture was extracted with ethyl acetate, and the extract was washed with water and dried (MgSO₄). After removal of the solvent, the residue was subjected to a column chromatography on silica-gel (40 g). From the eluate with hexane-ethyl acetate (1:1, v/v) was obtained 2-[4-[4-(4-fluorophenyl)-1-piperazinyl]butyl]-2H-1,4-benzothiazin-3(4H)-one. The yield was 293 mg (43.2%). Recrystallization from methanol gave prisms, m.p. 150°–151° C.

IR(Nujol)cm⁻¹: 3180, 1665.

NMR δ(ppm)in CDCl₃: 1.33–2.2(6H, m), 2.29–2.67(6H, m), 3.03–3.14(4H, m), 3.41(1H, d.d, J=6 and 8 Hz), 6.73–7.34(8H, m), 9.0 (1, broad).

Elemental Analysis for $C_{22}H_{26}FN_3OS$, Calcd.: C 66.14; H 6.56; N 10.43, Found: C 66.10; H 6.69; N 10.43.

EXAMPLES 39–44

By a process similar to that in Example 12, the compounds shown in Table 11 were obtained.

TABLE 11

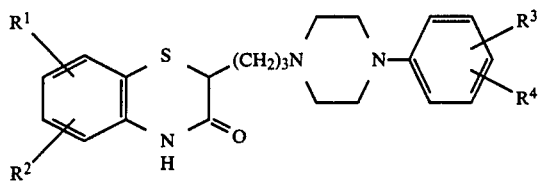

| Example No. | $R^1$ | $R^2$ | $R^3$ | $R^4$ | Melting point (°C.) (salt) | Recrystallization solvent | Yield (%) |
|---|---|---|---|---|---|---|---|
| 39 | H | 6-CH$_3$ | H | 4'-F | 158–160 2HCl | Methanol-dichloromethane | 60.0 |
| 40 | H | 7-CH$_3$ | H | 4'-F | 157–159 2HCl | Methanol | 45.4 |
| 41 | H | 5-C$_2$H$_5$ | H | 4'-F | 147–149 2HCl | Methanol-dichloromethane | 55.2 |
| 42 | 5-CH$_3$ | 6-CH$_3$ | H | 4'-F | 135–137 HCl.½H$_2$O | Ethanol-dichloromethane | 75.7 |
| 43 | 5-CH$_3$ | 8-CH$_3$ | H | 4'-F | 131–133 2HCl | Methanol | 57.9 |
| 44 | 6-CH$_3$ | 8-CH$_3$ | H | 4'-F | 138–139 2HCl | Methanol-dichloromethane | 49.3 |

EXAMPLE 45

In the same manner as Example 12, 6-(3-bromopropyl)-6H-1,3-dioxolo[4,5-g][1,4]benzothiazin-7(8H)-one was allowed to react with 1-(4-fluorophenyl)piperazine to give 6-[3-[4-(4-fluorophenyl)-1-piperazinyl]propyl]-6H-1,3-dioxolo[4,5-g][1,4]benzothiazin-7(8H)-one.dihydrochloride. The yield was 64.8%. m.p. 175°–177° C. (recrystallized from methanol-chloroform).

Elemental Analysis for C$_{22}$H$_{24}$FN$_3$O$_3$S.2HCl, Calcd.: C 52.59; H 5.22; N 8.36, Found: C 52.68; H 5.30; N 8.34.

EXAMPLE 46

In the same manner as Example 12, 2-(3-bromopropyl)-6,7-cyclopenteno-2H-1,4-benzothiazin-3(4H)-one was allowed to react with 1-(4-fluorophenyl)piperazine to give 6,7-cyclopenteno-2-[3-[4-(4-fluorophenyl)-1-piperazinyl]propyl]-2H-1,4-benzothiazin-3(4H)-one.hydrochloride. The yield was 35.1%. m.p. 135°–137° 1C. (recrystallized from ethanol-water).

Elemental Analysis for C$_{24}$H$_{28}$FN$_3$OS.HCl.½H$_2$O, Calcd.: C 61.19; H 6.42; N 8.92, Found: C 61.35; H 6.27; N 8.96.

EXAMPLE 47

In the same manner as Example 12, 3-(3-bromopropyl)-7,8,9,10-tetrahydro-1H-naphtho[2,1-b][1,4]thiazin-2(3H)-one was allowed to react with 1-(4-fluorophenyl)piperazine to give 3-[3-[4-(4-fluorophenyl)-1-piperazinyl]propyl]-7,8,9,10-tetrahydro-1H-naphtho[2,1-b][1,4]thiazin-2(3H)-one.hydrochloride. The yield was 60.6% m.p. 145°–147°C. (recrystallized from methanol-dichloromethane).

Elemental Analysis for C$_{25}$H$_{30}$FN$_3$OS.2HCl, Calcd.: C 58.59; H 6.29; N 8.20, Found: C 58.54; H 6.30; N 8.03.

EXAMPLE 48

Recrystallization of 2-[3-[4-(4-fluorophenyl)-1-piperazinyl]propyl]-5-methyl-2H-1,4-benzothiazin-3(4H)-one.dihydrochloride obtained in Example 12 from ethanol-water gave the corresponding hydrochloride, m.p. 189°–191° C.

Elemental Analysis for C$_{22}$H$_{26}$FN$_3$OS.HCl, Calcd.: C 60.51; H 6.53: N 9.57, Found: C 60.61; H 6.24; N 9.64.

EXAMPLE 49

In the same manner as Example 12, 2-(3-bromopropyl)-5-methyl-2H-1,4-benzothiazin-3(4H)-one was allowed to react with 1-(2-fluorophenyl)piperazine to give 2-{3-[4-(2-fluorophenyl)-1-piperazinyl]propyl}-5-methyl-2H-1,4-benzothiazin-3(4H)-one.dihydrochloride. The yield was 24.2%. m.p. 121°–123° C.

Elemental analysis for C$_{22}$H$_{26}$FN$_3$OS.2HCl.½H$_2$O, Calcd.: C 54.88; H 6.07; N 8.73, Found: C 55.12; H 5.76; N 8.44.

EXAMPLE 50

In the same manner as Example 12, 2-(3-bromopropyl)-5-methyl-2H-1,4-benzothiazin-3(4H)-one was allowed to react with 1-(3-fluorophenyl)piperazine to give 2-{3-[4-(3-fluorophenyl)-1-piperazinyl]propyl}-5-methyl-2H-1,4-benzothiazin-3(4H)-one.dihydrochloride. The yield was 37.2%. m.p. 132°–134° C.

Elemental analysis for C$_{22}$H$_{26}$FN$_3$OS.2HCl.½H$_2$O, Calcd.: C 54.88; H 6.07; N 8.73, Found: C 55.05; H 5.82; N 8.72.

Formulation Example

For use as an antihypertensive drug, the compound (I) of this invention can be used in the following exemplary formulation.

| | | |
|---|---|---|
| (1) 2-[3-[4-(4-Fluorophenyl)-1-piperazinyl]propyl]-5-methyl-2H—1,4-benzothiazin-3(4H)—one | | 5 g |
| (2) Lactose | | 95 g |
| (3) Corn starch | | 29 g |
| (4) Magnesium stearate | | 1 g |
| | 1000 Tablets | 130 g |

The whole amounts of (1) and (2) are mixed with 17 g of (3) and the mixture is granulated with a paste prepared from 7 g of (3). Then 5 g of (3) and the whole amount of (4) are added and the whole mixture is compression-molded on a compression tabletting machine to give 1000 tablets each containing 5 mg of (1).

Reference Example 1

To a solution of 3.06 g of 2-amino-4,5-dimethylthiophenol in 50 ml of dimethylformamide was added 5.48 g of methyl 2,5-dibromovalerate at room temperature with stirring. The mixture was stirred for 14 hours, poured into water, and extracted with ethyl acetate. The ethyl acetate layer was washed with water, dried (MgSO$_4$), and concentrated. The residue was washed with a mixture of ether and hexane to obtain 4.35 g (69.3%) of 2-(3-bromopropyl)-6,7-dimethyl-2H-1,4-benzothiazin-3(4H)-one as crystals. Recrystallization from methanol gave prisms, m.p. 151°–153° C.

IR(Nujol)cm$^{-1}$: 3200, 1660.

NMR δ(ppm)in CDCl$_3$: 1.37–2.27(4H, m), 2.42(6H, s), 3.23–3.4(1H, m), 3.37(2H, t, J=6 Hz), 6.64(1H, s), 7.03(1H, s), 8.9(1H, broad).

Elemental Analysis for C$_{13}$H$_{16}$BrNOS, Calcd.: C 49.69; H 5.13; N 4.46, Found: C 49.84; H 4.97; N 4.75.

Reference Examples 2–10

By a process similar to that in Reference Example 1, the compounds shown in Table 12 were obtained.

TABLE 12

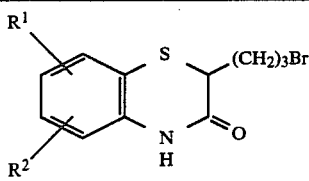

| Reference Ex. No. | R$^1$ | R$^2$ | Melting point (°C.) | Recrystallization solvent | Yield (%) |
|---|---|---|---|---|---|
| 2 | H | H | 103–104 | Ethyl acetate | 56.9 |
| 3 | H | 5-OCH$_3$ | 97–98 | Methanol | 40.0 |
| 4 | H | 7-OCH$_3$ | 100–101 | Ethyl acetate-hexane | 60.3 |
| 5 | H | 5-CH$_3$ | 72–73 | Ethyl acetate-hexane | 45.6 |
| 6 | H | 7-CH$_3$ | 126–127 | Ethyl acetate-hexane | 57.7 |
| 7 | H | 6-Cl | 146 | Methanol | 47.2 |
| 8 | H | 7-Cl | 140–141 | Ethyl acetate | 42.1 |
| 9 | H | 6-CF$_3$ | 149–150 | Ethyl acetate-hexane | 17.9 |
| 10 | 5-CH$_3$ | 7-CH$_3$ | 109–109 | Ethyl acetate | 70.9 |

Reference Example 11

To a solution of 4.6 g of 2-aminothiophenol in 50 ml of dimethylformamide was added dropwise 9.55 g of methyl 2,4-dibromobutyrate with stirring at room temperature. After stirring one hour, the reaction mixture was poured into water to give crystals of 2-(2-bromoethyl)-2H-1,4-benzothiazin-3(4H)-one. The crystals were collected by filtration and washed with water, n-hexane and cold methanol. The yield was 6.32 g (63.3%). Recrystallization from ethyl acetate gave prisms, m.p. 151°–152° C.

IR(Nujol)cm$^{-1}$: 3200, 1660.

NMR δ(ppm)in CDCl$_3$: 1.90–2.67(2H, m), 3.57(2H, t, J=6 Hz), 3.71(1H, d.d, J=6 and 8), 6.80–7.37(4H, m), 9.5(1H, broad).

Elemental Analysis for C$_{10}$H$_{10}$BrNOS, Calcd.: C 44.13; H 3.70; N 5.15, Found: C 44.03; H 3.54; N 5.13.

Reference Example 12

A solution of 3.10 g of 2-amino-5-methoxythiophenol and 5.20 g of methyl 2,4-dibromobutyrate in 30 ml of dimethylformamide was stirred at room temperature for 2 hours. The mixture was poured into ice-water and the resulting crystals were collected by filtration and washed with water. Recrystallization from methanol gave 3.94 g (65.2%) of 2-(2-bromoethyl)-7-methoxy-2H-1,4-benzothiazin-3(4H)-one as prisms, m.p. 142°–143° C.

IR(Nujol)cm$^{-1}$: 3190, 1650.

NMR δ(ppm)in CDCl$_3$: 1.87–2.63(2H,m), 3.60(2H, t, J=6), 3.68(1H, d.d, J=6 and 8), 3.76(3H, s), 6.63–6.92(3H, m), 9.62(1H, broad).

Elemental analysis for C$_{11}$H$_{12}$BrNO$_2$S, Calcd.: C 43.72; H 4.00; N 4.64, Found: C 44.09; H 3.60; N 4.52.

Reference Example 13

(1) To a suspension of 3.0 g of 2-ethoxycarbonyl-2H-1,4-benzothiazin-3(4H)-one in ethanol (50 ml) was added portionwise 0.95 g of sodium borohydride with stirring at room temperature. After stirring for 2 hours, the mixture was diluted with water, made acidic with acetic acid, and extracted with ether. The ether layer was washed with water, dried (MgSO$_4$), and then concentrated under reduced pressure. The residue was washed with hexane to obtain 1.25 g (50.8%) of 2-hydroxymethyl-2H-1,4-benzothiazin-3(4H)-one as crystals. Recrystallization from ethyl acetate gave prisms, m.p. 156°–157° C.

IR(Nujol)cm$^{-1}$: 3500–3300, 3200, 1670.

NMR δ(ppm)in DMSO—d$_6$: 3.41–3.74(3H, m), 5.09(1H, m), 6.83–7.33(4H, m), 10.83(1H, broad).

Elemental Analysis for C$_9$H$_9$NO$_2$, Calcd.: C 55.37; H 4.65; N 7.17, Found: C 55.39; H 4.68; N 7.29.

(2) To a solution of 1.0 g of 2-hydroxymethyl-2H-1,4-benzothiazin-3(4H)-one in 20 ml of chloroform was added 0.9 ml of thionyl chloride, and the mixture was heated for 2 hours under reflux. The mixture was concentrated under reduced pressure and the residue was extracted with ether. The extract was washed with water, dried (MgSO$_4$), and concentrated. The crude product was subjected to a column chromatography on silica-gel (40 g). From the eluate with hexane-ethyl acetate (4:1, v/v) was obtained 640 mg (58.7%) of 2-chloromethyl-2H-1,4-benzothiazin-3(4H)-one as crystals. Recrystallization from ethyl acetate and n-hexane gave needles, m.p. 152°–153° C.

IR(Nujol)cm$^{-1}$: 3190, 1660.

NMR δ(ppm)in CDCl$_3$: 3.6–3.93(3H, m), 6.89–7.37(4H, m), 9.4(1H, broad).

Elemental Analysis for C$_9$H$_8$ClNOS, Calcd.: C 50.59; H 3.77; N 6.55, Found: C 50.44; H 3.53; N 6.54.

Reference Example 14

By a process similar to that in Reference Example 13, 2-(2-hydroxyethyl)-2H-1,4-benzothiazin-3(4H)-one was allowed to react with thionyl chloride to give 2-(2-chloroethyl)-2H-1,4-benzothiazin-3(4H)-one. The yield was 72.7%. Recrystallization from methanol gave prisms, m.p. 133°–133.5° C.

IR(Nujol)cm$^{-1}$: 3200, 1660.

NMR δ(ppm)in CDCl$_3$: 1.72–2.57(2H, m), 3.59–3.87(3H, m), 6.84–7.35(4H, m), 9.64(1H, broad).

Elemental Analysis for C$_{10}$H$_{10}$ClNOS, Calcd.: C 52.75; H 4.43; N 6.15, Found: C 52.62; H 4.27; N 6.10.

Reference Example 15

(1) To a solution of 6.26 g of 2-aminothiophenol in 50 ml of dimethylformamide was added 9.85 g of 2-bromo 5-hydroxyvaleric acid. The mixture was stirred at room temperature for 2 hours and at 100° C. for 1 hour. The reaction solution was cooled, poured into water, and extracted with ethyl acetate. The ethyl acetate layer was washed with water, dried (MgSO$_4$) and then concentrated under reduced pressure. The concentrate was subjected to a column chromatography on silica-gel (200 g). From the eluate with hexane-acetone (2:1, v/v) was obtained 3.7 g (31.6%) of 2-(3-hydroxypropyl)-2H-1,4-benzothiazin-3(4H)-one as crystals. Recrystallization from ethyl acetate-hexane gave prisms, m.p. 59°–60° C.

IR(Nujol)cm$^{-1}$: 3500–3100, 3200, 1660.

NMR δ(ppm)in CDCl$_3$: 1.53–2.1(4H, m), 2.4(1H, broad), 3.37–4.02(3H, broad), 6.93–7.33(4H, m), 9.57(1H, broad).

Elemental Analysis for C$_{11}$H$_{13}$NO$_2$S, Calcd.: C 59.17; H 5.87; N 6.27, Found: C 58.83; H 5.81; N 6.53.

(2) By a process similar to that in Reference Example 13-(2), 2-(3-hydroxypropyl)-2H-1,4-benzothiazin-3(4H)-one was allowed to react with thionyl chloride to obtain 2-(3-chloropropyl)-2H-1,4-benzothiazin-3(4H)-one. The yield was 59.1%. Recrystallization from ethyl acetate-hexane gave prisms, m.p. 98°–99° C.

IR(Nujol)cm$^{-1}$: 3200, 1665.

NMR δ(ppm)in CDCl$_3$: 1.62–2.2(4H, m), 3.33–3.72(3H, m), 6.86–7.33(4H, m), 9.64(1H, broad).

Elemental Analysis for C$_{11}$H$_{12}$ClNOS, Calcd.: C 54.66; H 5.00; N 5.79, Found: C 54.51; H 4.84; N 5.74.

Reference Example 16

(1) To a solution of 2.86 g of 2-(3-bromopropyl)-2H-1,4-benzothiazin-3(4H)-one in 10 ml of dimethyl sulfoxide was added 0.54 g of sodium cyanide. The mixture was stirred at room temperature for 3 hours and diluted with water. The resulting crystals were collected by filtration and washed with water. Recrystallization from methanol gave 1.55 g (66.7%) of 2-(3-cyanopropyl)-2H-1,4-benzothiazin-3(4H)-one as prisms, m.p. 107°–108° C.

IR(Nujol)cm$^{-1}$ 3190, 2220, 1665(broad).

NMR δ(ppm)in CDCl$_3$: 1.62–2.22(4H, m), 2.23–2.45(2H, m), 3.35–3.50(1H, m), 6.85–7.35(4H, m), 9.17(1H, broad).

Elemental Analysis for C$_{12}$H$_{12}$N$_2$OS, Calcd.: C 62.05; H 5.21; N 12.06, Found: C 61.78; H 5.19; N 11.79.

(2) A mixture of 1.45 g of 2-(3-cyanopropyl)-2H-1,4-benzothiazin-3(4H)-one, 40 ml of 18.8% solution of hydrogen chloride in ethanol and 0.3 ml of water was heated under reflux for 24 hours. The reaction solution was cooled, diluted with water, and extracted with ether. The ether layer was washed with water, a saturated aqueous solution of sodium hydrogencarbonate and water in that order, then dried (MgSO$_4$). The solvent was evaporated off to obtain 1.60 g (91.4%) of 2-(3-ethoxycarbonylpropyl)-2H-1,4-benzothiazin-3(4H)-one. Recrystallization from ethyl acetate gave prisms, m.p. 78°–79° C.

IR(Nujol)cm$^{-1}$: 3200, 1730, 1660.

NMR δ(ppm)in CDCl$_3$: 1.21(3H, t, J=7 Hz), 1.5–2.2(4H, m), 2.31–2.47(2H, m), 3.32–3.51(1H, m), 3.44(2H, q, J=7 Hz), 6.72–7.39 (4H, m), 8.2(1H, broad).

Elemental Analysis for C$_{14}$H$_{17}$NO$_3$S, Calcd.: C 60.19; H 6.13; N 5.01, Found: C 60.33; H 6.03; N 5.44.

(3) To a suspension of 0.46 g of lithium aluminum hydride in 50 ml of ether was added dropwise, with ice-cooling, a solution of 1.6 g of 2-(3-ethoxycarbonylpropyl)-2H-1,4-benzothiazin-3(4H)-one in ether (30 ml). After the mixture was stirred for one hour, water was added dropwise thereto. The resultant white precipitates were filtered off, and the filtrate was dried (MgSO$_4$). The solvent was evaporated off, and the residue was subjected to a column chromatography on silica-gel (70 g). From the eluate with hexane-ethyl acetate (1:1, v/v) was obtained 0.75 g (55.6%) of 2-(4-hydroxybutyl)-2H-1,4-benzothiazin-3(4H)-one. Recrystallization from ethyl acetate gave prisms, m.p. 101°–102° C.

IR(Nujol)cm$^{-1}$: 3400–3150, 3210, 1660.

NMR δ(ppm)in CDCl$_3$: 1.44–2.1(6H, m), 1.80(1H, broad), 3.31–3.71(3H, m), 6.81–7.33(4H, m), 9.24(1H, broad).

Elemental Analysis for C$_{12}$H$_{15}$NO$_2$, Calcd.: C 60.73; H 6.37; N 5.90, Found: C 60.69; H 6.35; N 5.82.

(4) By a process similar to that in Reference Example 13-(2), 2-(4-hydroxybutyl)-2H-1,4-benzothiazin-3(4H)-one was allowed to react with thionyl chloride to obtain 2-(4-chlorobutyl)-2H-1,4-benzothiazin-3(4H)-one. The yield was 59.0%. m.p. 111°–112° C. (recrystallized from ethyl acetate-hexane).

IR(Nujol)cm$^{-1}$: 3190, 1665.

NMR δ(ppm)in CDCl$_3$: 1.47–2.06(6H, m), 3.33–3.57(3H, m), 6.86–7.34(4H, m), 9.67(1H, broad).

Elemental Analysis for C$_{12}$H$_{14}$ClNOS, Calcd.: C 56.35; H 5.52; N 5.48, Found: C 56.26; H 5.41; N 5.13.

Reference Example 17

(1) To a solution of 4.18 g of 2-(2-hydroxyethyl)-2H-1,4-benzothiazin-3(4H)-one in 50 ml of dimethylformamide, was added portionwise 0.8 g of 60% sodium hydride in oil with stirring under ice-cooling. After the mixture was stirred for 10 minutes, 1.24 ml of methyl iodide was added thereto. The temperature of the reaction system was then reverted to room temperature and the mixture was stirred for one hour. After dilution with water, the mixture was extracted with ethyl acetate. The ethyl acetate layer was washed with water, dried (MgSO$_4$) and concentrated under reduced pressure. The residue was subjected to a column chromatography on silica-gel (50 g). From the eluate with hexane-using silica-gel (50 g). From the eluate with hexane-ethyl acetate (2:1, v/v) was obtained 3.90 g (87.4%) of 2-(2-hydroxyethyl)-4-methyl-2H-1,4-benzothiazin-3(4H)-one as an oily substance.

IR(Nujol)cm$^{-1}$: 3600–3250, 1660(broad).

NMR δ(ppm)in CDCl$_3$: 1.62–2.31(2H, m), 2.47(1H, broad), 3.43(3H, s), 3.61(1H, t, J=7 Hz), 3.77(2H, m), 6.90–7.41(4H, m).

(2) To a solution of 4.90 g of 2-(2-hydroxyethyl)-4-methyl-2H-1,4-benzothiazin-3(4H)-one in 20 ml of dichloromethane, was added dropwise 5 ml of thionyl chloride with stirring at room temperature. The mixture was stirred for one hour and then concentrated. The concentrate was subjected to a column chromatography on silica-gel (35 g). From the eluate with hexane-ethyl acetate (4:1, v/v) was obtained 5.05 g (95.3%) of 2-(2-chloroethyl)-4-methyl-2H-1,4-benzothiazin-3(4H)-one as an oily substance.

IR(neat)cm$^{-1}$: 1660.

NMR δ(ppm)in CDCl$_3$: 1.83–2.55(2H, m), 3.46(3H, s), 3.56–3.76(1H, m), 3.70(2H, t, J=6 Hz), 6.91–7.43(4H, m).

Reference Example 18

A solution of 2.78 g of 2-methylaminothiophenol and 5.48 g of methyl 2,5-dibromovalerate in 100 ml of dimethylformamide was stirred at 50° C. for 2 hours. The reaction solution was poured into cold water and extracted with ether. The extract was washed with water, dried (MgSO$_4$), and concentrated.

The residue was subjected to a column chromatography on silica-gel (150 g). From the eluate with hexane-ethyl acetate (4:1, v/v) was obtained 4.57 g (76.2%) of 2-(3-bromopropyl)-4-methyl-2H-1,4-benzothiazin-3(4H)-one as an oily substance.

IR(neat)cm$^{-1}$: 1660.

NMR δ(ppm)in CDCl$_3$: 1.53–2.23(4H, m), 3.31–3.5(3H, m), 3.44(3H, s), 6.91–7.40(4H, m).

Reference Examples 19–23

By a process similar to that in Reference Example 1, the following compounds were obtained.

TABLE 13

| Reference Example No. | R$^1$ | R$^2$ | Melting point | Recrystallization solvent | Yield (%) |
|---|---|---|---|---|---|
| 19 | H | 6-CH$_3$ | 154–155 | Methanol-dichloromethane | 37.7 |
| 20 | H | 5-C$_2$H$_5$ | 74–75 | Methanol | 47.8 |
| 21 | 5-CH$_3$ | 6-CH$_3$ | 95–96 | Ethyl acetate-hexane | 19.1 |
| 22 | 5-CH$_3$ | 8-CH$_3$ | Oily substance | — | 95.5 |
| 23 | 6-CH$_3$ | 8-CH$_3$ | 131–132 | Ethyl acetate | 54.0 |

Reference Example 24

By a process similar to that in Reference Example 1, 2-amino-4,5-methylenedioxythiophenol was allowed to react with methyl 2,5-dibromovalerate to give 6-(3-bromopropyl)-6H-1,3-dioxolo[4,5-g][1,4]benzothiazin-7(8H)-one. The yield was 45.0%. m.p. 168°–169° C. (recrystallized from methanol-dichloromethane).

Reference Example 25

By a process similar to that in Reference Example 1, 2-amino-4,5-cyclopentenothiophenol was allowed to react with methyl 2,5-dibromovalerate to give 2-(3-bromopropyl)-6,7-cyclopenteno-2H-1,4-benzothiazin-3(4H)-one. The yield was 44.3%. m.p. 178°–179° C. (recrystallized from methanol-dichloromethane).

Reference Example 26

By a process similar to that in Reference Example 1, 1-amino-5,6,7,8-tetrahydro-2-thionaphthol was allowed to react with methyl 2,5-dibromovalerate to give 3-(3-bromopropyl)-7,8,9,10-tetrahydro-1H-naphtho[2,1-b][1,4]thiazin-2(3H)-one. The yield was 38.2%. m.p. 122°–123° C. (recrystallized from methanol).

What is claimed is:

1. A 1,4-benzothiazine derivative of the formula;

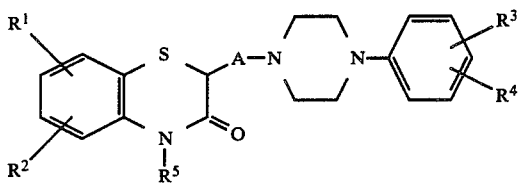

wherein R$^1$ and R$^2$ independently stand for hydrogen, halogen, a lower alkyl group, a lower alkoxy group or trifluoromethyl group, or R$^1$ and R$^2$, taken together, form a 5–7 membered ring represented by

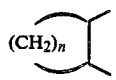

wherein n is an integer of 3 to 5 or a 5–6 membered ring represented by

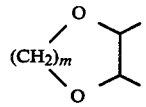

wherein m is 1 or 2, R$^3$ and R$^4$ independently stand for hydrogen, halogen, a lower alkyl group, a lower alkoxy group or trifluoromethyl group, R$^5$ stands for hydrogen or a lower alkyl group, and A stands for an alkylene group or a pharmaceutically acceptable salt thereof.

2. A 1,4-benzothiazine derivative as claimed in claim 1, wherein R$^1$ and R$^2$, taken together, form a 5–7 membered ring represented by

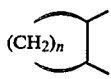

wherein n is an integer of 3 to 5.

3. A 1,4-benzothiazine derivative as claimed in claim 1, wherein R$^1$ and R$^2$, taken together, form a 5–6 membered ring represented by

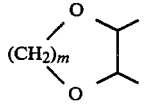

wherein m is 1 or 2.

4. A 1,4-benzothiazine derivative as claimed in claim 1, wherein at least one of R$^3$ and R$^4$ stands for fluorine.

5. A 1,4-benzothiazine derivative as claimed in claim 1, wherein R$^5$ stands for hydrogen.

6. A 1,4-benzothiazine derivative as claimed in claim 1, wherein A stands for ethylene.

7. A 1,4-benzothiazine derivative as claimed in claim 1, wherein A stands for trimethylene.

8. A 1,4-benzothiazine derivative as claimed in claim 1, wherein at least one of $R^1$ and $R^2$ stands for a lower alkyl group and at least one of $R^3$ and $R^4$ stands for fluorine substituted at the 4-position of the benzene ring.

9. A 1,4-benzothiazine derivative as claimed in claim 1, wherein $R^1$ and $R^2$, taken together, form a 5–7 membered ring represented by

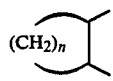

wherein n is an integer of 3 to 5, and at least one of $R^3$ and $R^4$ stands for fluorine.

10. The 1,4-benzothiazine derivative as claimed in claim 1, which is 6,7-cyclopenteno-2-[3-[4-(4-fluorophenyl)-1-piperazinyl]propyl]-2H-1,4-benzothiazine-3(4H)-one.

11. The 1,4-benzothiazine derivative as claimed in claim 1, which is 2-[3-[4-(4-fluorophenyl)-1-piperazinyl]-propyl]-5-methyl-2H-1,4-benzothiazine-3(4H)-one.

12. A pharmaceutical composition suitable for prevention or treatment of hypertension or ischemic cardiovascular disease which comprises, an effective amount of a 1,4-benzothiazine derivative or its pharmaceutically acceptable salt as defined in claim 1, and a pharmaceutically acceptable carrier or diluent therefor.

13. A method for prevention or treatment of hypertension or ischemic cardiovascular disease which comprises administering to a patient an effective amount of a 1,4-benzothiazine derivative or a pharmaceutically acceptable salt thereof of the formula:

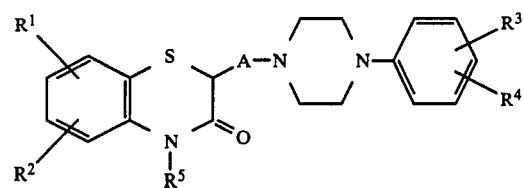

$R^1$ and $R^2$ independently stand for hydrogen, halogen, a lower alkyl group, a lower alkoxy group or trifluoromethyl group, or $R^1$ and $R^2$, taken together, form a 5–7 membered ring represented by

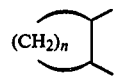

wherein n is an integer of 3 to 5 or a 5–6 membered ring represented by

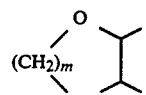

wherein m is 1 or 2, $R^3$ and $R^4$ independently stand for hydrogen, halogen, a lower alkyl group, a lower alkoxy group or trifluoromethyl group, $R^5$ stands for hydrogen or a lower alkyl group, and A stands for an alkylene group.

* * * * *